United States Patent
Fujii et al.

(10) Patent No.: US 7,406,191 B2
(45) Date of Patent: Jul. 29, 2008

(54) INSPECTION DATA PRODUCING METHOD AND BOARD INSPECTION APPARATUS USING THE METHOD

(75) Inventors: Yoshiki Fujii, Fukuchiyama (JP); Toshiyuki Sugiyama, Fukuchiyama (JP)

(73) Assignee: Omron Corporation, Kyoto-shi (JP)

( * ) Notice: Subject to any disclaimer, the term of this patent is extended or adjusted under 35 U.S.C. 154(b) by 722 days.

(21) Appl. No.: 10/633,594

(22) Filed: Aug. 5, 2003

(65) Prior Publication Data
US 2004/0076323 A1    Apr. 22, 2004

(30) Foreign Application Priority Data
Aug. 6, 2002    (JP) .............................. 2002-228181

(51) Int. Cl.
  *G06K 9/00*    (2006.01)
(52) U.S. Cl. ................... 382/144; 382/145; 382/147; 382/148; 382/151; 382/152
(58) Field of Classification Search ................ 382/141, 382/142, 143, 144, 145, 146, 147, 148, 149, 382/150, 151, 152; 348/86–87, 92, 94, 95, 348/125–137, 140–141, 143–147
See application file for complete search history.

(56) References Cited
U.S. PATENT DOCUMENTS 4,953,100 A     8/1990  Yotsuya
5,555,316 A  *  9/1996  Tsujikawa et al. ........... 382/150
5,724,439 A  *  3/1998  Mizuoka et al. ............. 382/149
5,822,449 A  * 10/1998  Kobayashi et al. .......... 382/141
5,991,435 A  * 11/1999  Tsujikawa et al. ........... 382/147
6,167,149 A  * 12/2000  Tsujikawa et al. ........... 382/147
6,278,797 B1 *  8/2001  Nagasaki et al. ............ 382/146

FOREIGN PATENT DOCUMENTS

| | | |
|---|---|---|
| DE | 43 39 715 C | 4/1995 |
| JP | 04-326049 | 11/1992 |
| JP | 06-082228 | 3/1994 |
| JP | 09-145334 | 6/1997 |

\* cited by examiner

*Primary Examiner*—Brian Q Le
(74) *Attorney, Agent, or Firm*—Foley & Lardner LLP (57) ABSTRACT

After a CAD data and a parts library are combined to produce an inspection data, the set data for the inspection window is automatically corrected using the image of a bare board for a board to be inspected. In this correcting process, an inspection window based on the aforementioned inspection data is set on a bare board image, and then an image in the inspection window W4 making up a reference for setting other windows is binarized, and lands 35 on this binary image are detected. Further, on the basis of the detection result, the set position and size of land windows W1 for solder inspection are corrected, after which the set positions of other inspection windows W2 to W4 are corrected.

11 Claims, 8 Drawing Sheets

INSPECTION DATA PRODUCING METHOD AND BOARD INSPECTION APPARATUS USING THE METHOD

BACKGROUND OF THE INVENTION

1. Field of the Invention

The present invention relates to a technique of processing an image obtained of a board with parts mounted thereon (hereinafter referred to as "the parts mounted board") and inspecting the soldered state of parts on a board and the mounted state of parts and electrodes on the board, or in particular to a technique for producing inspection data for this type of inspection.

2. Description of the Prior Art

In carrying out this type of inspection automatically, it is necessary to set various inspection data (this setting process is hereinafter referred to as "the teaching") for each part on the board, including the set data for the inspection window corresponding to the particular part (including the data indicating the set position and the size of the window), a parameter required to extract an image pattern in the inspection window (binary threshold value, etc.), a program for processing the extracted image pattern (hereinafter referred to as "the inspection program") and a criterion for determining whether the result of the processes is proper or not.

Generally, an inspection window for a plurality of portions including a land, a part and an electrode is set for each type of component part. Also, the parameter, the inspection program and the criterion described above are set for each window (the data and the program set for each of these windows is hereinafter referred to as "the inspection reference data"). Further, the inspection data for each part is made into a file and registered in a memory of the board inspection apparatus (this file is hereinafter referred to as "the inspection data file")

In the conventional board inspection apparatus, a parts library with inspection data registered therein for each part type is registered. The user executes for each part the process of designating the mounting position of the part on a model board image in a satisfactory mounting state, and attaching at a designated position the inspection data read from the parts library. In this way, an inspection data file can be efficiently produced.

Further, the teaching can be automated using the board design data such as the CAD data. In this case, the control unit of the inspection apparatus extracts the mounting position and the item number data of the particular part from the design data, reads the inspection data corresponding to the item number data from the parts library and sets the inspection data at the mounting position (Japanese Unexamined Patent Publication No. 5-35849).

The lands on the board are required to be designed taking into consideration various factors including the mounting condition of the electrodes and the heat radiation of the board in operation. The land size, therefore, is different for a different design rule. Some makers have no unified design rule and have different land sizes for different boards. Even those makers having a unified design rule sometimes set a plurality of land sizes based on old and new rules, or set different land sizes for different board sizes. Further, manufacturers fabricating a board on consignment for a plurality of makers are required to produce and inspect boards having various sizes of lands in view of the fact that the design rule varies from one maker to another.

The parts library described above is produced using a board image based on a predetermined design rule. In the case where a board changed in land size due to a different design rule is inspected, however, the situation may not be met by the inspection data in this parts library. In such a case, according to the prior art, the inspection windows are displayed in superposed relation on the image of a reference board after producing an inspection data file, and the user is caused to correct the position and size of the window manually. This correcting job consumes a great amount of time (the correction of a single board may consume about one half of a day). Thus, the burden on the user increases, and the inspection cannot be started early.

SUMMARY OF THE INVENTION

The present invention is developed in view of this problem, and an object of the invention is to automate the process for correcting the set data of an inspection window, and thereby greatly reducing the time and labor required for teaching, make it possible to start the board inspection at an early time.

Another object of the invention is to improve the utility of the teaching by making it possible to easily produce a parts library in the case where the board design rule is changed or a new design rule is added.

The inspection data producing method according to the invention consists in producing the inspection data for inspecting a board with parts mounted thereon by image processing. The inspection data corresponding to each part on a board to be inspected is read from the parts library produced in advance, and set at the mounting position of the particular part. After that, an image area corresponding to a land is detected on the image picked up from a model of the board to be inspected, and based on the result of this inspection, the set data for the inspection window included in the inspection data is corrected.

In the aforementioned case, the inspection data includes at least the set data for the inspection window. An inspection window may be set for each part, but preferably should be set for a plurality of portions including lands.

Further, the inspection data may include an inspection reference data used for inspection within the inspection window.

In the process of recovering the inspection data from the parts library and setting them at the mounting positions of the parts, the inspection data is read out in accordance with the operation of designating the particular inspection data in the parts library, and in accordance with the operation of designating the part mounting position on the board image, the inspection data thus read out can be set at the designated mounting position. As an alternative, based on the parts information obtained from the board design data such as the CAD data, the inspection data corresponding to each part can be automatically set at the mounting position of the particular part. In any case, the set position of the inspection window in the inspection data is converted in accordance with the part mounting position. As for the inspection reference data used for each inspection window, however, the data having the same contents as the inspection data of the parts library is basically used.

According to the invention, in the case where the setting of the inspection window by the inspection data set at a part mounting position fails to correspond to the land size of the actual board, the set data of the inspection window can be automatically corrected by a model image of the board to be inspected. In correcting the setting of the inspection window, therefore, the user simply produces a model board and picks up an image of the model board, thereby greatly reducing the time and labor required on the part of the user for correction.

The board to be inspected used for the correcting process is preferably a bare board before mounting the parts thereon.

In the case where a plurality of inspection windows are set, the process of correcting the set data described above is preferably executed in such a manner that at least the inspection window for the lands is corrected preferably to include the whole image of the lands in the particular window. Further, in accordance with this correction, the set data for other inspection data can also be corrected.

In the inspection data producing method described above according to a preferred embodiment of the invention, the process for detecting an image area corresponding to a land includes the process executed for searching the land edge positions with reference to a solder inspection window (the land inspection window) based on the uncorrected set data on the model image described above. The board model is required to be formed with a conductor pattern satisfactorily as a prerequisite. Even in the case where the land size fails to correspond to the solder inspection window, therefore, the land will probably never be displaced greatly from the particular window. In other words, at least a part of the land is considered to be located within the particular window.

Once the land edge positions are searched with reference to the solder inspection window, therefore, the possibility of a pattern detection error except for lands is reduced. Thus, the image area for the lands can be detected with high accuracy and the correcting process can be executed properly.

In the inspection data producing method according to another preferred embodiment of the invention, the inspection reference data corresponding to the corrected inspection window is corrected in accordance with the correction of the set data for the inspection window.

In the case where the land size is changed, for example, a corresponding solder fillet may be changed. With this change, the criterion for determining the appropriateness of the fillet is required to be also corrected. According to this embodiment, the correction of the inspection reference data can be automatically carried out. Therefore, the time and labor required for the correcting process can be further reduced.

For this type of correction, however, it is necessary to lay down a rule for introducing the inspection reference data suitable for the sizes of various inspection windows in advance.

In the inspection data producing method according to still another embodiment of the invention, the inspection data for the same type of parts as a predetermined part on the board is corrected using the inspection data corrected for the particular predetermined data. Generally, the same type of parts are mounted according to the same rule, and therefore have the same land size. In the case where there are a plurality of parts of the same type on the board, therefore, the correction for one part is applicable to the correction for other parts in the same way. This embodiment is based on this technical concept and can further improve the efficiency at which the inspection data are corrected.

The same type of parts as described herein are defined as parts to which the same inspection data is applicable in the parts library and can include a plurality of parts of different item numbers. This definition applies to the entire description that follows. The correction of the inspection data, which may be limited to the set data for the inspection window, can also include the correction of the inspection reference data, as applicable to the whole description that follows.

In the inspection data producing method according to yet another embodiment of the invention, the inspection data shared by all the parts of the same type on the board is produced using the inspection data corrected for the same parts, so that the inspection data for each part is rewritten to the common set data described above.

According to this embodiment, even in the case where the inspection data obtained individually for the parts are varied one from another, a common inspection data free of this variation can be produced and applied to the parts. The common inspection data can be produced by determining the average value for all the inspection data. Nevertheless, a common inspection data may alternatively be produced by extracting the inspection data for which the difference of the set values is included in a predetermined range and determining an inspection data of an intermediate value in the range.

Further, according to the invention, after the aforementioned correcting process, the parts library may be rewritten or a new parts library can be produced using the corrected inspection data for predetermined parts. By doing so, even in the case where the board design rule is changed or new board design rule is introduced, the teaching executed once using the existing parts library makes it possible to easily rewrite the existing parts library or produce a new library by use of the inspection data produced by the particular teaching.

A board inspection apparatus according to the invention comprises an image input means for inputting an image picked up from a board, a data file producing means for reading the inspection data corresponding to each part from a parts library produced in advance for the board to be inspected and setting the inspection data at the mounting position of the same part thereby to produce the inspection data file required for board inspection, a land detection means for receiving a model input image of a corresponding board after complete production of the inspection data file and detecting an image area corresponding to the land on the same image, a correcting means for correcting the set data for the inspection window in accordance with the detected image area, and a registration means for registering the inspection data file including the corrected set data in a memory.

In this board inspection apparatus, the image input means (which may be supplied with a digital image in some cases) is configured of an A/D converter and an interface for receiving the image signal from the imaging means for picking up an image of the board. The board of which an image is picked up is mainly a board having parts mounted thereon. Nevertheless, a bare board may alternatively be imaged at the time of correcting the inspection window.

The parts library can be registered in the internal memory of the apparatus. Nevertheless, the parts library can be read out alternatively from a removable medium such as a flexible disk or a CD-ROM.

The data file producing means receives the operation of selecting a predetermined inspection data of the parts library and the operation of designating the position of a part on a model image of the parts-mounted board input from the image input means. Then, the data file producing means reads the selected inspection data from the parts library and sets the selected inspection data at the designated part mounting position. As an alternative, the data file producing means can receive the input of the CAD data and set the inspection data corresponding to each part at the mounting position of the particular part indicated by the CAD data.

The inspection data file produced above is not necessarily a single file but may be a mass of a plurality of files. Also, a common file may be set for the data such as an inspection program shared by a plurality of types of parts, and a link to the common file may be set.

The land detection means receives the image input from the image input means as a model image of the board after complete production of the inspection data file, and thus can start the process of detecting an image area. This land detection means is preferably configured in such a manner as to start the process of receiving the image after receiving a predetermined command input. Also, in the process of detecting an image area corresponding to edges, preferably, a solder inspection window is set on the model image based on the inspection data and the land edge positions are searched with reference to the particular window.

The inspection data file including the corrected set data may be registered in an external memory or a removable storage medium as well as in the internal memory of the apparatus.

Assume that a board having a different design rule is inspected anew by the board inspection apparatus having the aforementioned configuration. After producing an inspection data file using the existing parts library, the set data for the inspection window in this inspection data file is automatically corrected using the model image of the board and the corrected inspection data file is registered. After that, the inspection is conducted, in which the image of the board to be inspected is received from the image input unit, and an inspection window based on the registered inspection data file is set on this image. In this way, the inspection of each part can be carried out.

This board inspection apparatus may further comprise a second correcting means for correcting the inspection reference data corresponding to the corrected inspection window in accordance with the correction of the set data for the inspection window.

Further, the board inspection apparatus according to the invention can comprise means for receiving the operation of selecting the inspection data for a predetermined part from the corrected inspection data file and rewriting the corresponding inspection data of the existing parts library by the selected inspection data. As an alternative, a new parts library can be produced from the selected inspection data and registered in an internal or external memory.

The rewrite operation or the new registration described above may use either all or a part of the inspection data in the inspection data file.

Further according to the invention, there is also provided a board inspection apparatus having such a function that the inspection data produced by use of the existing parts library are corrected to an inspection data corresponding to a new board design rule by an image input means, a data file producing means, a land detection means and a correcting means similar to those described above. In this inspection data producing apparatus, the inspection data file including the corrected inspection data is stored in a predetermined storage medium or transmitted through a communication line.

DESCRIPTION OF THE PREFERRED EMBODIMENTS

Figure 1:
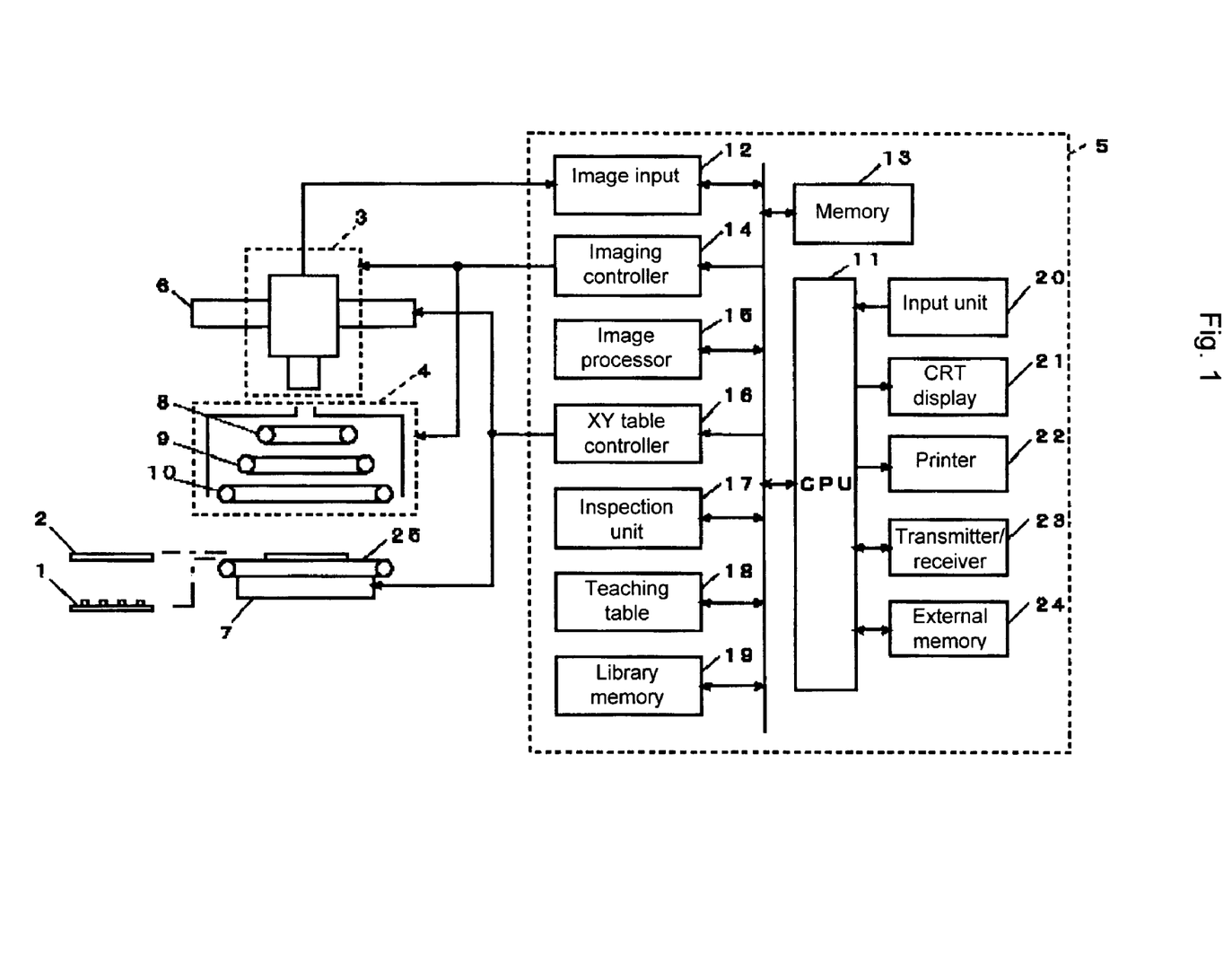
FIG. 1 is a block diagram showing a configuration of a board inspection apparatus according to an embodiment of the invention.

FIG. 1 shows a configuration of a board inspection apparatus according to an embodiment of the invention.

This board inspection apparatus determines whether the soldered portions, etc. on the board are satisfactory or not by processing an image obtained from a board to be inspected, and comprises an imaging unit 3, a light projection unit 4, a control unit 5, an X-axis table unit 6 and a Y-axis table unit 7.

In FIG. 1, numeral 1 designates a board to be inspected (hereinafter sometimes referred to as "the object board 1"), and numeral 2 a bare board with no parts mounted thereon as yet which is used at the time of teaching before inspection.

The Y-axis table unit 7 includes a conveyor 25 for supporting the boards 1, 2. The conveyor 25 is driven by a motor not shown to move the boards 1, 2 along Y axis (in the direction perpendicular to the page). The X-axis table unit 6, on the other hand, moves, while supporting, the imaging unit 3 and the light projection unit 4 along X axis (lateral direction in the drawing) above the Y-axis table 7.

The light projection unit 4 is configured of three annular light sources 8, 9, 10 having different diameters. These light sources 8, 9, 10 are adapted to emit red, green and blue light, respectively, and are arranged at different angles of elevation as viewed from the supporting surfaces of the boards 1, 2 by setting the centers thereof just above the observation point.

The imaging unit 3 is a CCD camera for generating a color image, and has the optical axis thereof set in a position corresponding to the centers of the light sources 8, 9, 10 along the vertical direction. As a result, the light reflected from the boards 1, 2 to be observed enters the imaging unit 3 and, being converted into the three primary color signals R, G, B, are input to the control unit 5.

The control unit 5 is a computer with the CPU 11 as a main component, and has a configuration including an image input unit 12, a memory 13, an imaging controller 14, an image processor 15, an XY table controller 16, an inspection unit 17, a teaching table 18, a library memory 19, an input unit 20, a CRT display unit 21, a printer 22, a transmitter/receiver 23 and an external memory unit 24.

The image input unit 12 includes an amplifier circuit for amplifying the image signals of R, G, B from the imaging unit 3 and an A/D converter for converting the image signals into digital signals. The memory 13 has set therein an image storage area for storing a gray scale image data in digital amount for each color and a binary image obtained by binalizing the gray scale image. This memory 13 is used also to temporarily hold various data and programs at the time of teaching or inspection.

The imaging controller 14 includes an interface for connecting the imaging unit 3 and the light projection unit 4 to the CPU 11, and has the function of adjusting the light amount of each light source of the light projection unit 4 and maintaining the balance between the color outputs of the imaging unit 3 in compliance with an instruction from the CPU 11.

The XY table controller 16 includes an interface for connecting the X-axis table unit 6 and the Y-axis table unit 7 to the CPU 11, and controls the motion of the X-axis table unit 6 and the Y-axis table unit 7 in compliance with an instruction from the CPU 11.

The teaching table 18 is for storing an inspection data file required for inspecting each of various boards. Each inspection data file has set therein a binary threshold value required to extract the set position and size of the inspection window for each part mounted on a corresponding board and the color patterns of R, G, B in the particular inspection window (including a binary threshold value of brightness as well as a binary threshold value for each color component), an inspection program used for the inspection window and inspection data such as criteria. Further, the teaching table 18 can store therein the data used for the teaching process, including a binary threshold value for detecting a land on the image.

The library memory 19 is for storing a parts library in which the inspection data shared by the boards are registered for each type of the parts. This parts library is edited by the work to correct the preset default inspection data in accordance with the actual image of the parts. Each inspection data is registered in correspondence with the variation name of the parts or the item number of the CAD data.

The inspection data file is read by the CPU 11, set in the memory 13 or the like and supplied to the image processor 15 and the inspection unit 17 at the time of inspection.

The image processor 15 extracts, pixel by pixel, the luminance values of R, G, B and the brightness from each image data of R, G, B stored in the memory 13. Also, the image processor 15 binarizes the image data in each inspection window and extracts the color patterns of R, G, B sequentially based on the inspection data file. Further, the image processor 15 extracts a predetermined feature amount from the color patterns based on the inspection program described above.

The inspection unit 17 executes the inspection process on each inspection window by comparing the result of extraction of the feature amount with a reference value or otherwise. The CPU 11 determines whether the object inspection board 1 is satisfactory or not from the overall inspection result for each inspection window. The result of this final determination is output to the CRT display unit 21, the printer 22 or the transmitter/receiver 23.

The input unit 20 is for inputting the various conditions for inspection and the inspection information, and configured of a keyboard and a mouse. The CRT display unit 21 (hereinafter referred to simply as "the display unit 21") is supplied with the image data and the inspection result from the CPU 11 and the input data or the like from the input unit 20, and displays them on the display screen. Also, the printer 22 is supplied with the inspection result or the like from the CPU 11 and prints them out in a predetermined format.

The transmitter/receiver 23 is for exchanging the data between a parts mounting machine, a soldering machine and other devices. With regard to the inspection object board 1T determined as defective, for example, the identification information and the contents of the defect are transmitted to a correcting unit in the subsequent stage, thereby making it possible to correct the defective portion rapidly.

The external memory unit 24 is a device for reading/writing data from/into a recording medium such as a CD•R or an magnetooptic disk. The external memory unit 24 is used for storing the inspection result and recovering the CAD data or the like at the time of teaching.

The CAD data can alternatively be retrieved from an external system using the transmitter/receiver 23.

In the aforementioned configuration, the image processor 15 and the inspection unit 17 is configured of an exclusive processor having built therein a program for executing each process described above. Nevertheless, an exclusive processor is not always required, but the functions of the image processor 15 and the inspection unit 17 may be added to the CPU 11 used for main control. Also, the memory 13, the teaching table 18 and the library memory 19 are not necessarily physically separated from each other, but may be set in the same memory (such as a hard disk).

In the board inspection apparatus according to this embodiment, the CAD data constituting the design data of the board to be inspected is retrieved from the external memory unit 24 before inspection. The CAD data and the data registered in the parts library are combined with each other to produce an inspection data file automatically. Further, in the board inspection apparatus according to this embodiment, the process of adjusting the inspection window by the produced inspection data file is automatically executed using the image of a bare board.

Figure 2:
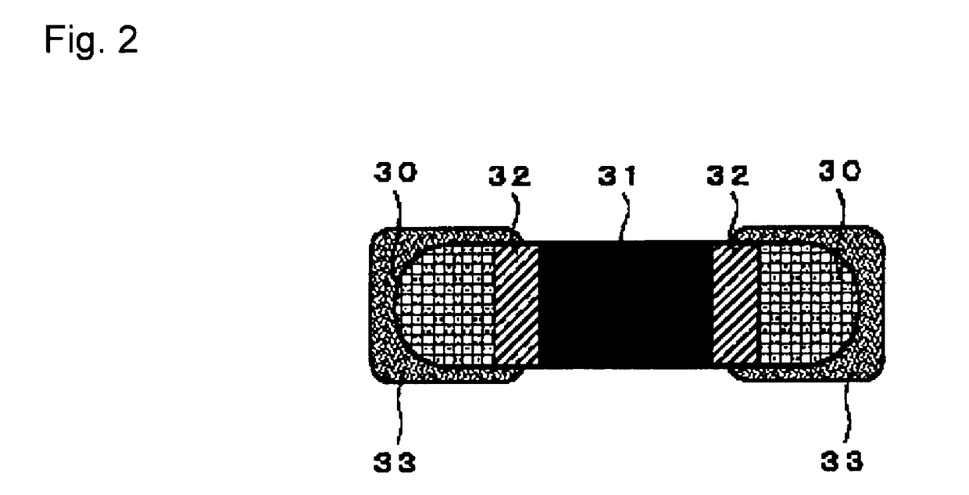
FIG. 2 is a diagram schematically showing the appearance of a chip part.

FIG. 2 schematically shows a configuration of a chip part as an example of a part. In FIG. 2, reference numeral 30 designates solder, numeral 31 a part proper, numeral 32 electrodes and numeral 33 lands. An image of these component parts picked up by an optical system of FIG. 1 shows that a color pattern corresponding to an inclination angle of each component part appears at a position corresponding to the solder and the electrodes on the image thus obtained.

Figure 3:
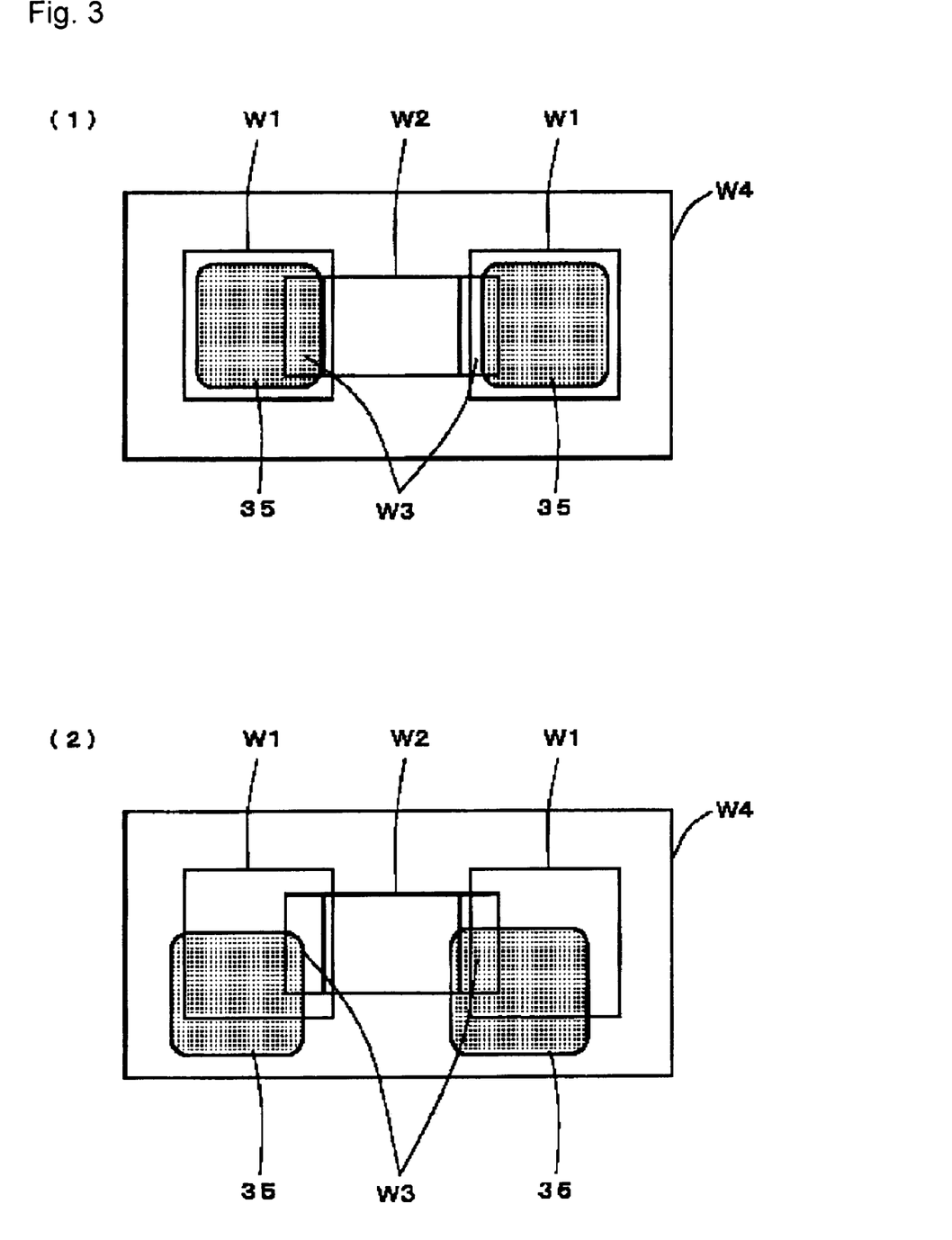
FIG. 3 is a diagram showing an example in which the setting of an inspection window is suited to a land on the image and an example in which such setting is not suited to a land on the image.

FIG. 3(1) shows a state in which an inspection window is properly set on the chip part. In FIG. 3(1), numeral 35 designates lands on the image, while the images of the solder 30, the part proper 31 and the electrodes 32 are not shown.

In FIG. 3(1), character W1 designates an inspection window corresponding to the lands 35. The inspection window W1 sets the center position of the lands 35 while at the same time containing the entire lands 35 (the window W1 is hereinafter referred to as "the land window W1"). This land window W1 is used mainly for solder inspection.

Character W2 designates an inspection window for the part proper and is used for detecting a drop-off or an inclination, if any, of the part. Character W3, on the other hand, designates inspection windows for the electrodes. These windows are used for detecting a defect such as a rise of the electrodes with respect to the solder.

Further, a fourth inspection window W4 containing the inspection windows described above is set for this part. This inspection window W4 provides a reference for setting the other windows W1 to W3 in position (the window W4 is hereinafter referred to as "the reference window W4"). At the time of teaching, for example, the set position of the reference window W4 is established based on the part mounting positions indicated by the CAD data, after which the set positions of the other inspection windows W1 to W3 are established (this is also the case with inspection). Further, the reference window W4, as described later, functions also as a processing area for detecting the land edge position in the process for correcting the set data of the land windows W1.

FIG. 3(2) shows an example of a state in which the inspection windows W1 to W4 similar to those shown in FIG. 3(1) are not suitable for the part. The lands 35 in this example are displaced from the assumed position of the land window W1 and somewhat appear larger than in the case of FIG. 3(1).

As shown in FIG. 3(2), in the case where the lands on the image cease to be contained within the land window W1 and are displaced from the land window W1, the inspection would be undesirably conducted on a different portion than the portion to be inspected. In the process of adjusting the inspection window described above, this inconvenience is obviated by correcting the set data of the land window W1 and in accordance with this correction, the set data of the other inspection windows W2 to W4 are also corrected.

A specific example of correction of the set data for the land window W1 will be explained.

In the board inspection apparatus according to this embodiment, an optimal binary threshold value for detecting the lands 35 on the image is set beforehand in accordance with the color of the conductor pattern of the board and registered in the teaching table 18 or the like. According to this embodiment, the image of the bare board is binarized using this binary threshold value, and the resulting binary image is used for correcting the inspection window.

According to this embodiment, the binary image in the reference window W4 is projected along X and Y axes, and positions corresponding to the edges of the lands 35 are detected on a histogram obtained by this projection process. Based on the result of this detection, the set position and the size of the land window W1 are corrected.

Figure 4:
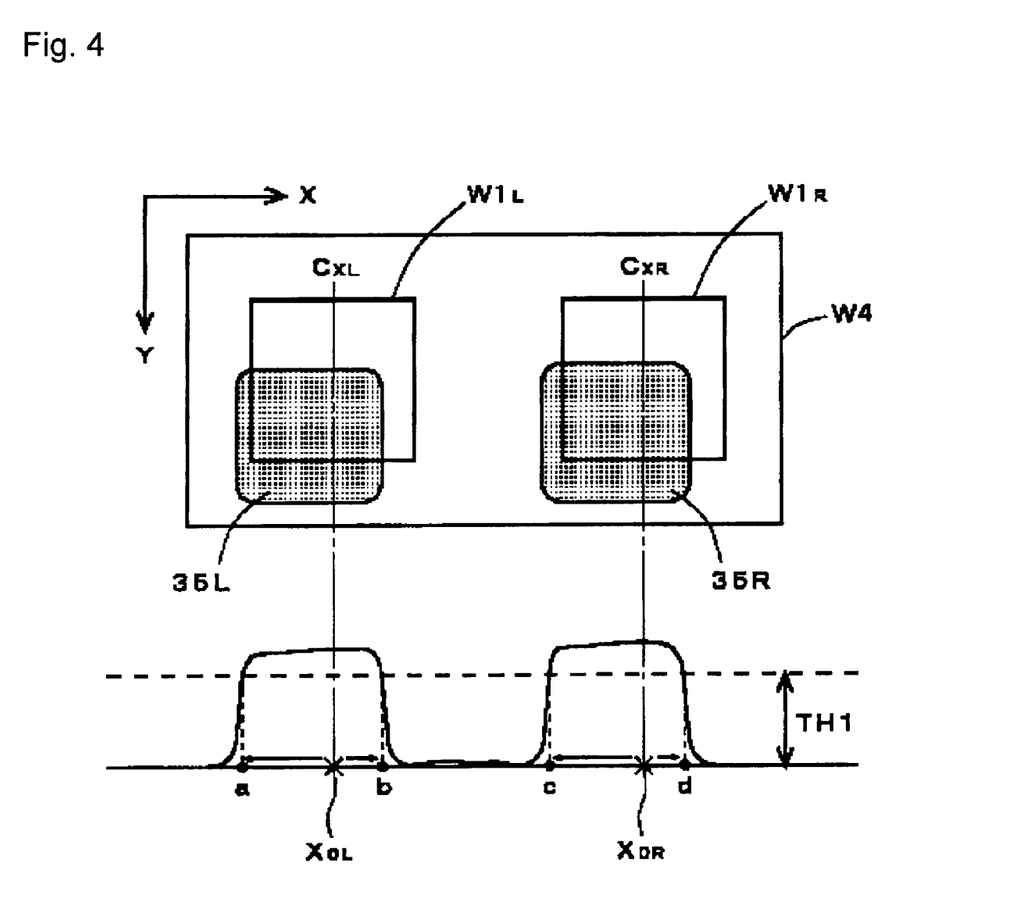
FIG. 4 is a diagram showing a specific example of the process for detecting land edges.
Figure 5:
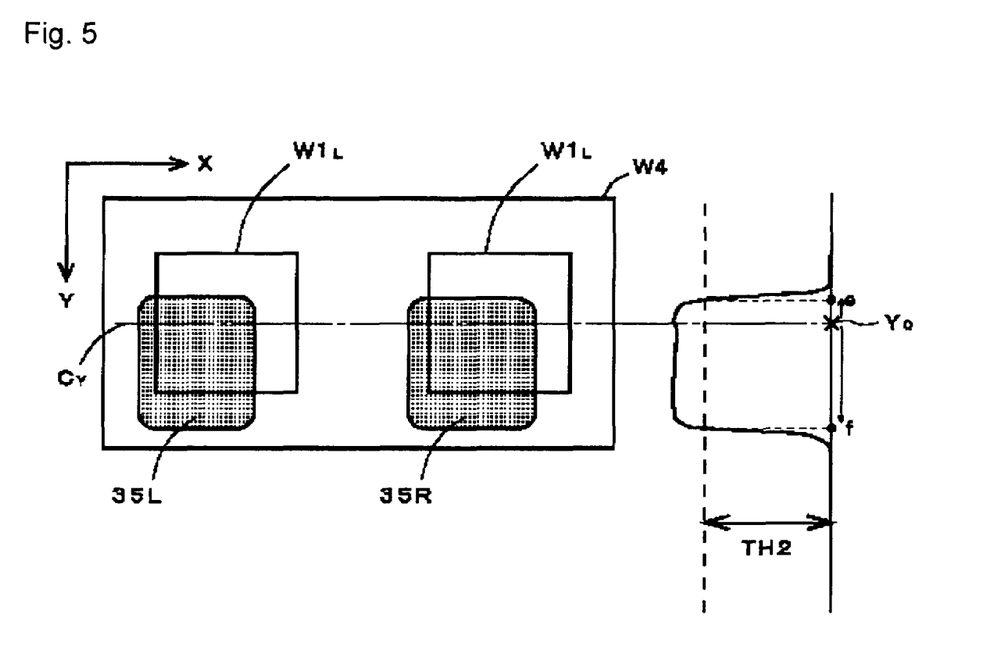
FIG. 5 is a diagram showing a specific example of the process for detecting land edges.

FIGS. 4 and 5 show specific examples of the process for detecting the edges of the lands 35. In these diagrams, only the reference window W4 and the land window W1 are shown among the inspection windows. The left and right land windows are denoted by different symbols $W1_L$ and $W1_R$, respectively. In similar fashion, the land images are designated by different reference numerals 35L, 35R.

In FIG. 4, the left and right edges of the land windows $W1_L$, $W1_R$ are detected using a histogram while projecting two binary images in the reference window W4 on X axis. Specifically, the histogram described above is searched in left and right directions from the origin points $X_{OL}$, $X_{OR}$ corresponding to the center lines $C_{XL}$, $C_{XR}$ along X axis for each of the windows $W1_L$, $W1_R$ thereby to detect the positions where the number of projection pixels decreases. Thus, the left edge position of the lands 35L, 35R can be specified by the points a, c detected by the leftward search, and the right edge position of the lands 35L, 35R by the points b, d detected by the rightward search.

In FIG. 5, the binary image in the reference window W4 is projected on Y axis, and using the histogram thus obtained, the upper and lower edges of the land windows $W1_L$, $W1_R$ are detected. In FIG. 5, the left and right lands 35L, 35R are aligned substantially at the same height, and therefore the projection process for these lands 35L, 35R are executed at the same time. After that, in the histogram obtained by the projection process, the positions where the number of projection pixels decreases are detected by upward and downward search starting from an origin point $Y_0$ corresponding to the center line $C_Y$ along Y axis of the land windows $W1_L$, $W1_R$. The upper edge position of the lands is specified by the point e detected by upward search, while the lower edge position of the lands is specified by the point f detected by downward search.

According to this embodiment, in order to detect the decrease in the number of projection pixels, predetermined threshold values TH1, TH2 (TH2 corresponds to a value equal to the double of the transverse width of a land) are set from the actual longitudinal and transverse widths of the land, and a boundary point where the number of projection pixels at each position transfers from an area where it exceeds the threshold values TH1, TH2 to an area where it decreases below the same threshold values.

In this type of correcting process, a bare board formed with a conductor pattern satisfactorily based on the design data should be selected, and therefore the displacement of the lands 35L, 35R occurring in the image of the bare board is not very large. Thus, the upper, lower, left and right edges of the lands 35L, 35R are rarely displaced beyond the center lines $C_{XL}$, $C_{XR}$, $C_Y$ of the land windows $W1_L$, $W1_R$. Therefore, the number of projection pixels at the search start points $X_{OL}$, $X_{OR}$, $Y_0$ is considered to exceed the threshold values TH1, TH2.

According to the method shown in FIGS. 4 and 5, therefore, the search process is conducted from within the lands 35L, 35R toward the ends thereof. Thus, the four edges of the lands 35L, 35R can be positively detected. Also, according to this method, even in the case where a noise source pattern exists at a place distant from the land windows $W1_L$, $W1_R$, this pattern is not erroneously detected as a land. Therefore, the edges can be detected with a higher accuracy.

As described above, once the lands 35L, 35R on the image are clarified from the detected edges, the set position and size of the land windows $W1_L$, $W1_R$ are changed to contain the lands 35L, 35R. Further, in accordance with this change, the set positions of the other inspection windows W2 to W4 are also changed. Thus, the inspection data suitable for the board design rule can be set.

The method of correcting the set data for the inspection window is not limited to the method described above. As an alternative, for example, the method disclosed in Japanese Unexamined Patent Publication No. 9-145334 may be used, in which the land edge positions are detected by projection after correcting the displacement of the land window W1, and based on the detection result, the set position and size of the land window are adjusted.

Figure 6:
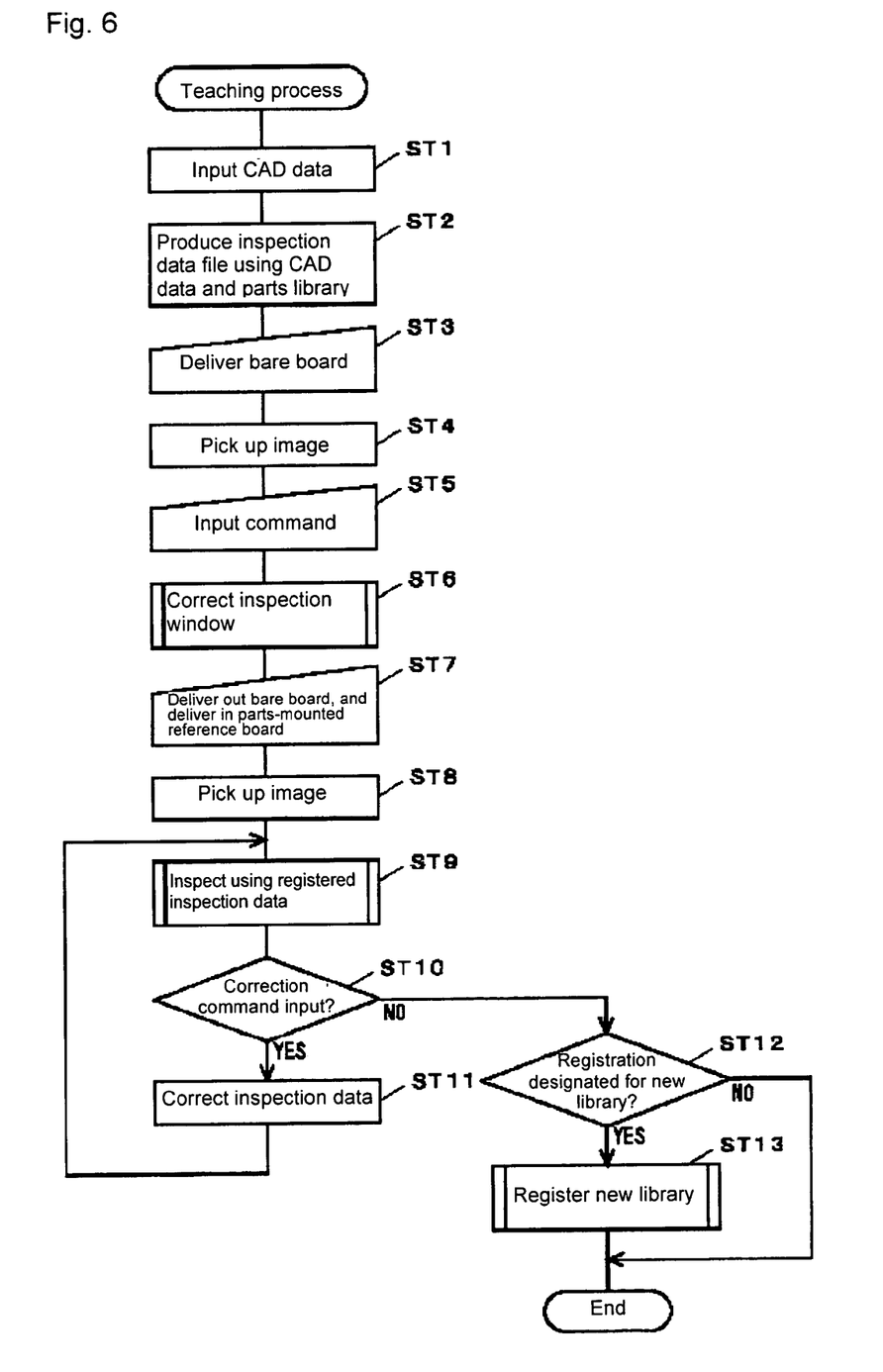
FIG. 6 is a flowchart showing the steps of the teaching process.

FIG. 6 shows a series of steps of the teaching process for the board inspection apparatus. In the description that follows, each step is described as "ST".

This process is started when a storage medium storing the CAD data of the board to be taught is set in an external memory unit 24 and the read operation is started by the operator. In step ST1, the CPU 11 reads the CAD data from the storage medium and inputs it in the working area of the memory 13. For each part mounting position indicated by the CAD data, the corresponding inspection data is read from the parts library in recognition of the mounted part, and the process of setting the inspection data at the mounting position is repeated. This process produces a prototype of the inspection data file.

Next, in step ST3, the operator delivers the bare board 2 onto the conveyor 25 using a board conveyor not shown. In the next step ST4, the bare board begins to be imaged in accordance with the delivery process. Further, in step ST5 when a predetermined command is input, the process proceeds to step ST6 for executing the process of correcting the inspection window.

Figure 7:
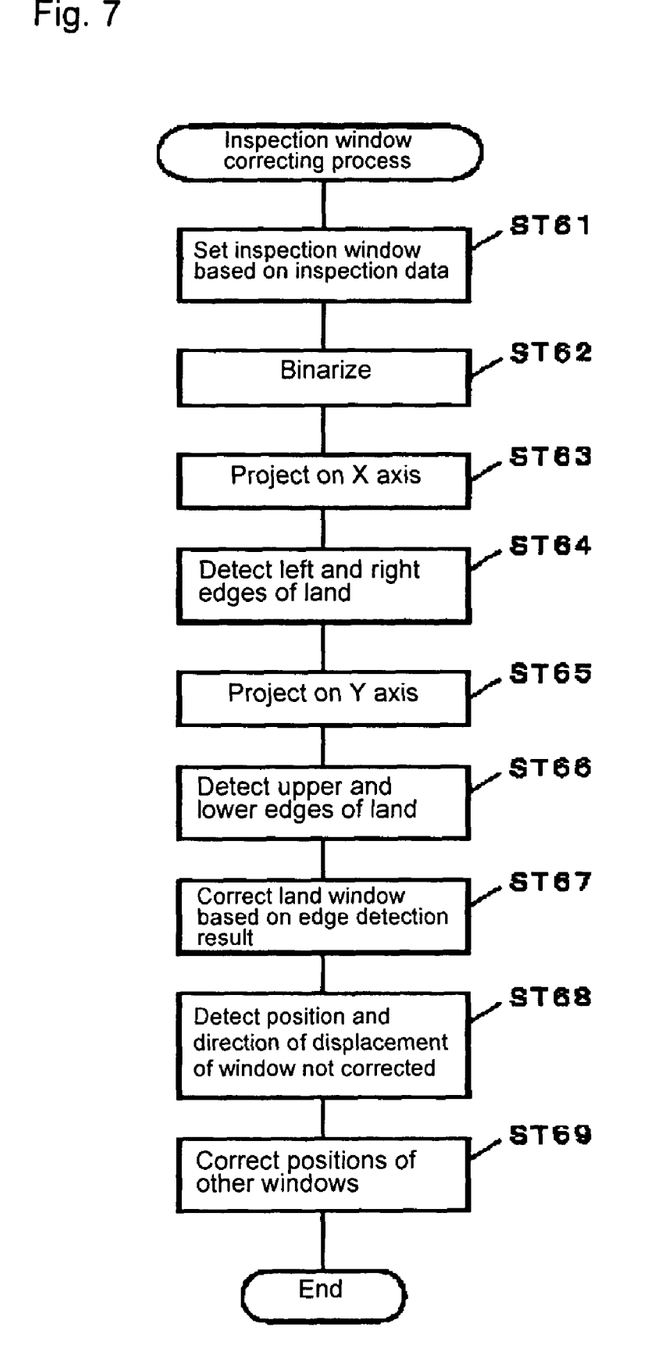
FIG. 7 is a flowchart showing the steps of correcting the inspection window for a given part.

FIG. 7 shows the process of correcting the inspection windows for a single component part.

First, in step ST61, the inspection windows for a particular part are set based on the inspection data produced. Next, in step ST62, the image within the reference window W4 is binarized among the inspection windows set as described above.

For binarization, the operator is required to input the type of the conductor pattern for a bare board to be processed, and set a threshold value (taught in advance) in accordance with the input data.

In the next steps ST63 to ST66, the binary image is projected for each of X and Y axes, and in the histogram thus obtained, the edge positions of the lands 35 on the image are detected by a search process executed with reference to the center line of the land window W1. In the case where a plurality of lands 35 to be processed are arranged along a coordinate axis in the detecting process, as shown in FIG. 4, the search process is executed for each land 35. In the case where the lands 35 to be processed are aligned along the direction perpendicular to a particular coordinate axis, on the other hand, as shown in FIG. 5, the search process for the lands 35 in alignment is executed collectively.

Upon detection of the edge positions of the lands 35 this way, the size and the center position of the lands 35 are specified based on the edge detection result in step ST67, and in accordance with this detection result, the set position and size of the land windows W1 are corrected.

After that, in step ST68, the amount and direction of displacement of the land windows W1 are detected by use of the coordinate of each center point of the land windows W1 before and after correction. Further, in the next step ST69, in accordance with the amount and direction of the displacement thus detected, the other inspection windows W2 to W4 are moved thereby to correct the set positions of these windows.

Returning to FIG. 6, upon complete processing of the steps shown in FIG. 7 for each part, the operator removes the bare board and in place thereof, delivers a model of the parts mounting board to be inspected (hereinafter referred to as "the reference board") onto the conveyor 25 in step ST7.

This reference board is for testing whether the inspection data produced by the aforementioned process is proper or not. When the reference board begins to be imaged in step ST8, the inspection data for the parts are sequentially read out and the inspection is conducted (ST9).

The operator checks the inspection result on the display unit 21, and determines whether the inspection data is required to be corrected or not. In the case where the operator determines that the correction is necessary, a correction command designating the part to be corrected is input.

With this input, the answer in step ST10 turns "YES", and the process proceeds to step ST11, where the inspection data for the designated part is corrected. This correcting process is executed using the image of the reference board. In the case where the set position and/or the size of the inspection windows W1 to W4 is required to be corrected, the present windows are displayed on the image, and the operator is rendered to conduct the job of correcting the set position and/or the size, as the case may be. Based on the result of this correcting job, the set data of the inspection windows are rewritten. In the case where the binarized threshold value is required to be corrected, the operator is caused to designate the desired color pattern to be extracted on the gray scale image, so that the binary threshold value is extracted from the image data at the designated place to replace the old threshold value. In the case where the criterion is required to be corrected, the operator is caused to designate an optimum pattern on the binary image, and by extracting the feature amount for the particular pattern or otherwise, a new criterion can be produced.

The process of correcting the inspection data by the test described above has been conventionally executed.

After completing an inspection data file usable for inspection by the series of process described above, a command is input to register a new library. Then, the process proceeds from ST12 to ST13 where the process of registering a new library is executed.

In this registration process, the inspection data liable to be used also for other boards is designated in the inspection data file, and a new parts library is produced with the designated inspection data. The inspection data can be freely designated. Also, all the inspection data in the inspection data file can be designated.

According to the process of steps shown in FIGS. 6 and 7, the inspection data automatically produced by the CAD data and the existing parts library can be automatically corrected using the bare board image. Thus, the operator labor and the time required for correction can be greatly reduced, and the teaching process can be executed efficiently. In addition, a new parts library can be produced from the inspection data corrected to the proper state. In the case where the board design rule is changed or a new design rule is introduced, therefore, a parts library conforming with the particular rule can be easily produced.

In registering a parts library anew, the existing parts library that has thus far been used for producing the inspection data file before correction is left as it is. Nevertheless, the inspection data of the existing parts library may alternatively be rewritten using the corrected inspection data file. In the case where the user has a plurality of board design rules, a parts library for each design rule may be produced by new registration in the method according to the embodiments described above. By the process of rewriting the existing parts library, a parts library having the inspection data suitable for the latest design rule shared by the boards can be easily produced in the case where the design rule is changed for a plurality of types of boards. In this way, the parts library required by the user can be easily produced, and therefore the utility of the teaching is improved, thereby further improving the teaching efficiency.

After completing the inspection data file in keeping with the board design rule in this way, assume that the board 1 to be inspected is conveyed on the conveyor 25 and imaged. Then, the control unit 5 sets the various inspection windows W1 to W4 for the parts on the image to be processed, and carries out the inspection using the inspection reference data corresponding to each window. In this inspection, assume that the mounting position of the parts is displaced. According to the method disclosed in Japanese Unexamined Patent Publication No. 9-145334 described above, the inspection is conducted after adjusting the set position of each inspection window based on the land position on the image.

Further, the design of the board inspection apparatus can be changed as described below.

First, unlike in the aforementioned embodiments in which the inspection windows are corrected after the inspection data file is automatically produced by the CAD data and the parts library, a similar correction can alternatively be carried out also in the case where the user reads the inspection data from the parts library and attaches them on the board image.

With the correction of the set data for the inspection windows, the inspection reference data corresponding to the corrected windows can also be corrected. As an example, an explanation will be given below about a case in which the criterion for determining the appropriateness of the fillet length is corrected in accordance with the correction of the size of the land windows W1.

Figure 8:
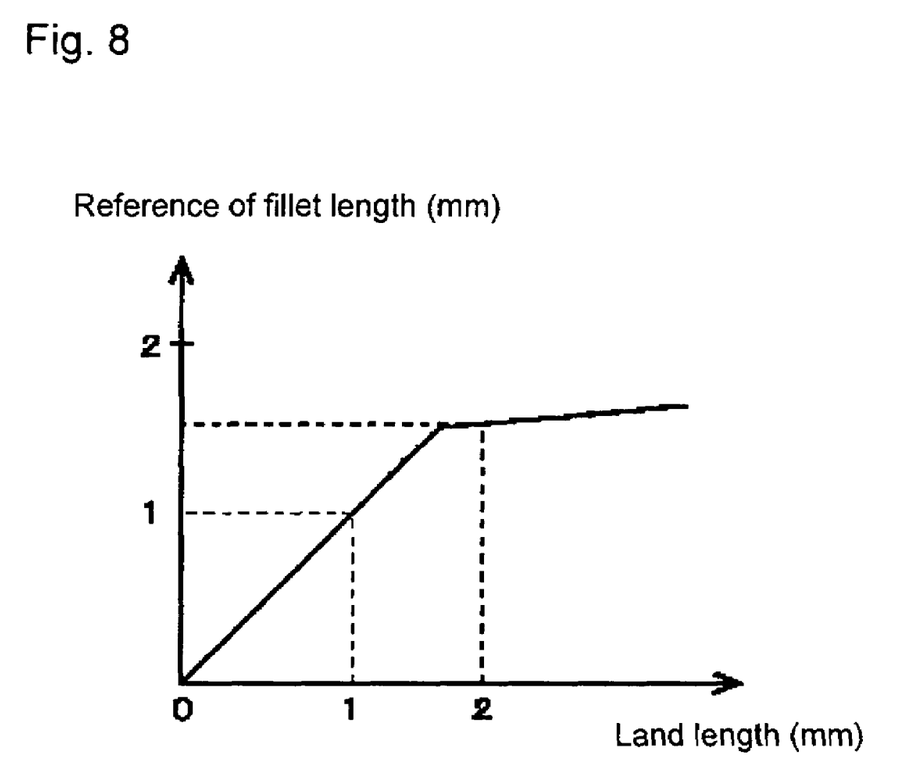
FIG. 8 is a graph showing the relation between land length and fillet length.

In the case where a large land is designed to radiate heat for a part which generates heat in operation, for example, the particular part is designed in such a way that the fillet length thereof is not changed simply in the same manner as the land size, but as shown in FIG. 8, the fillet length changes at a slower rate than the land size from a predetermined length. In this way, the fillet length, like the land window, depends to a large measure on the board design rule. Once the correction of the criterion is automated, therefore, the burden on the user can be further reduced, thereby further improving the teaching efficiency.

For correcting the criterion of the fillet length automatically, the relation between the land length and the fillet length shown in FIG. 8 is required to be determined and registered in advance as a correction rule in the teaching table 18 or the memory 13. In the case where the land windows W1 are corrected at the time of teaching, the length of the corrected land windows W1 is governed by the corrected rule. In this way, the fillet length suitable for the land windows W1 can be acquired and is used to rewrite the criterion.

In FIG. 8, the term "the land length" on the abscissa is defined as the land size along the longitudinal direction of the fillet. Also, the correction rule shown in FIG. 8 is desirably set for each part type. In the case where there is no sizable difference in the relation between the land length and the fillet length, however, a common correction rule may be set for a plurality of types of parts.

Further, with the board inspection apparatus described above, the inspection data can be unified for the same type of parts on the board by introducing any of the methods described below.

In one method, after correcting the inspection data for predetermined parts, the inspection data thus corrected are reflected in other parts of the same type. As another method, after correction for the parts of the same type, the average size of the land windows after correction is determined, and based on the average value thus determined, the set data for each part is rewritten (a similar method can be used also for a criterion).

According to the invention, in the case where a board design rule is changed or a new board design rule is introduced whereby the land size of a part is changed, the inspection data produced using the existing parts library can be automatically corrected. Thus, the time and labor consumed for teaching can be greatly reduced, and the board inspection can be started at an early time. Especially, the user such as a manufacturer on consignment who uses a multiplicity of design rules can efficiently proceed with the teaching work for various boards, and therefore the productivity can be improved by the resulting shorter processing time required for board inspection.

Also, according to the invention, in the case where a design rule is changed or a new board rule is added, the parts library can be rewritten or a new parts library can be produced easily. The user, therefore, can easily acquire the parts library as required, thereby improving the utility of teaching considerably.

This application claims priority from Japanese Patent Application 2002-228181, filed Aug. 6, 2002, which is incorporated herein by reference in its entirety.

What is claimed is:

1. A method of producing inspection data for inspecting a parts-mounted board by image processing, comprising:
   reading inspection data corresponding to each part on a board constituting an object of inspection from a parts library produced in advance;
   setting the inspection data at a mounting position of the part;
   detecting an image area corresponding to each land on an image picked up from a model of the board constituting the object of inspection; and
   based on the detection result, automatically correcting the set data for setting an inspection window included in the read inspection data, when the inspection window is displaced with respect to the image area corresponding to each land, so that the inspection window is adapted for inspection of the board;
   storing, as a correction rule, a relationship between a fillet length for a part and a land size for a part; and
   changing, based on the correction rule, a fillet length for the part at a slower rate than a land size for the part, when the design rule change occurs,
   wherein the inspection window is adapted due to a design rule change for one or more of the parts mounted on the board.

2. An inspection data producing method according to claim 1,
   wherein, in accordance with the correction of the set data of the inspection window, inspection reference data corresponding to the inspection window is corrected.

3. An inspection data producing method according to claim 1,
   wherein, using the corrected inspection data for a predetermined part on the board, inspection data for parts of the same type as the predetermined part is corrected.

4. An inspection data producing method according to claim 1,
   wherein the inspection data shared by the parts is produced using the inspection data corrected for the same type of parts on the board, and the inspection data for each part in rewritten into the common inspection data.

5. An inspection data producing method according to claim 1,
   further comprising the step of:
   rewriting the parts library or producing a new parts library for a predetermined part using the corrected inspection data.

6. An inspection data producing method according to claim 1, wherein the inspection data includes luminance and brightness values of Red, Green and Blue light shined on the part when mounted on the board.

7. An inspection data producing method according to claim 1, wherein, after the inspection window has been corrected using the image of the board in which no parts are mounted thereon, the method comprises:
   imaging a second model of the board in which parts are mounted thereon; and
   determining, based on the imaging of the second model of the board, whether the corrected inspection data is proper.

8. An inspection data producing method according to claim 1, wherein the inspection window is corrected using the image picked up from the model of the board on which no parts have been mounted.

9. An inspection data producing method according to claim 1, wherein the inspection data is automatically corrected when the image area corresponds to each land on the model of the board has been either increased or decreased with respect to the read inspection data.

10. An inspection data producing method according to claim 1, wherein the inspection window includes a first inspection window that encompasses the part itself, a second inspection window that encompasses solder regions used to mount the part on the board, and a third inspection window that encompasses land regions where the part is mounted on the board, and a reference inspection window for the part that encompasses regions covered by the first, second and third inspection windows.

11. A method of producing inspection data for inspecting a parts-mounted board by image processing, comprising:
   reading inspection data corresponding to each part on a board constituting an object of inspection from a parts library produced in advance;
   setting the inspection data at a mounting position of the part;
   detecting an image area corresponding to each land on an image picked up from a model of the board constituting the object of inspection; and based on the detection result, automatically correcting the set data for setting an inspection window included in the read inspection data, when the inspection window is displaced with respect to the image area corresponding to each land, so that the inspection window is adapted for inspection of the board;

wherein the step of detecting the image area corresponding to the land comprises:

retrieving the position of the land edges with reference to a solder inspection window based on the set data before correction on the image of the model, wherein left and right boundaries of the land edges are determined by using a histogram while projecting a plurality of binary images in a reference window on a first axis; and wherein top and bottom boundaries of the land edges are determined by using the histogram while projecting a plurality of binary images in the reference window on a second axis orthogonal to the first axis.

* * * * *